United States Patent [19]

Tyagi et al.

[11] Patent Number: 6,150,097
[45] Date of Patent: Nov. 21, 2000

[54] NUCLEIC ACID DETECTION PROBES HAVING NON-FRET FLUORESCENCE QUENCHING AND KITS AND ASSAYS INCLUDING SUCH PROBES

[75] Inventors: Sanjay Tyagi, New York; Fred Russell Kramer, Riverdale, both of N.Y.

[73] Assignee: The Public Health Research Institute of the City of New York, Inc., New York, N.Y.

[21] Appl. No.: 08/990,176

[22] Filed: Dec. 12, 1997

Related U.S. Application Data

[63] Continuation of application No. PCT/US97/06208, Apr. 14, 1997, which is a continuation-in-part of application No. PCT/US97/06532, Apr. 12, 1997.
[60] Provisional application No. 60/015,409, Apr. 12, 1996.
[51] Int. Cl.[7] .............................. C12Q 1/68; C07H 21/04
[52] U.S. Cl. .............................. 435/6; 435/810; 436/164; 436/172; 436/800; 536/24.3; 536/24.31; 536/24.32
[58] Field of Search .................. 435/6, 810; 436/164, 436/172, 800; 536/24.3, 24.31, 24.32

[56] References Cited

U.S. PATENT DOCUMENTS

| | | | |
|---|---|---|---|
| 4,261,968 | 4/1981 | Ullman et al. | 424/8 |
| 4,725,536 | 2/1988 | Fritsch et al. | 435/6 |
| 4,725,537 | 2/1988 | Fritsch et al. | 435/6 |
| 4,752,566 | 6/1988 | Collins et al. | 435/6 |
| 4,766,062 | 8/1988 | Diamond et al. | 435/6 |
| 4,822,733 | 4/1989 | Morrison | 435/6 |
| 5,082,830 | 1/1992 | Brakel et al. | 514/44 |
| 5,118,801 | 6/1992 | Lizardi et al. | 536/27 |
| 5,210,015 | 5/1993 | Gelfand et al. | 435/6 |
| 5,241,060 | 8/1993 | Engelhardt et al. | 536/27 |
| 5,260,433 | 11/1993 | Engelhardt et al. | 536/23 |
| 5,332,659 | 7/1994 | Kidwell | 435/6 |
| 5,348,853 | 9/1994 | Wang et al. | 435/6 |
| 5,487,972 | 1/1996 | Gelfand et al. | 435/6 |
| 5,491,063 | 2/1996 | Fisher et al. | 435/6 |
| 5,532,129 | 7/1996 | Heller | 435/6 |
| 5,538,848 | 7/1996 | Livak et al. | 435/5 |
| 5,565,322 | 10/1996 | Heller | 435/6 |
| 5,571,673 | 11/1996 | Picone | 435/6 |
| 5,622,821 | 4/1997 | Selvin et al. | 435/6 |
| 5,824,473 | 10/1998 | Meade et al. | 435/6 |

FOREIGN PATENT DOCUMENTS

| | | |
|---|---|---|
| 57754/86 | 11/1986 | Australia . |
| 0 070 685 A2 | 1/1983 | European Pat. Off. . |
| 0 232 967 A2 | 8/1987 | European Pat. Off. . |
| 0 286 898 A3 | 10/1988 | European Pat. Off. . |
| 0 364 255 A2 | 4/1990 | European Pat. Off. . |
| 0 601 889 A2 | 6/1994 | European Pat. Off. . |
| 0 640 828 A1 | 3/1995 | European Pat. Off. . |
| 0 745 690 A2 | 12/1996 | European Pat. Off. . |
| 5-123195 | 5/1993 | Japan . |
| WO 95/13399 | 5/1995 | WIPO . |

OTHER PUBLICATIONS

B.C. Bagwell, et al., "A New Homogeneous Assay System For Specific Nucleic Sequences: Poly–dA and Poly–A Detection," Nucleic Acids Research 22: 2424–2425 (1994).

J. Brand, et al., "Fluorescence Probes For Structure," Ann Rev Biochemistry 41: 843–868 (1972).

K.J. Breslauer, et al., "Predicting DNA Duplex Stability From The Base Sequence," P.N.A.S. (U.S.A.) 83: 3746–3750 (1986).

(List continued on next page.)

Primary Examiner—Carla J. Myers
Attorney, Agent, or Firm—Fish & Richardson PC

[57] ABSTRACT

Nucleic acid hybridization probes having a first conformation when not interacting with a target and a second conformation when interacting with a target, and having the ability to bring a label pair into touching contact in one conformation but not the other, are labeled with a non-FRET pair of chromophores and generate a fluorescent or absorbance signal. Kits may include such probes, and assays, including multiplex assays, may utilize such probes.

47 Claims, 7 Drawing Sheets

OTHER PUBLICATIONS

C.R. Cantor, et al., "Techniques For The Study Of Biological Structure And Function," (W.H. Freeman and Co., San Francisco) (U.S.A.) pp. 448–455 (1980).

C.R. Cantor, "Lighting Up Hybridization," Nature Biotechnology 14: 264 (1996).

Cardullo, et al., "Detection Of Nucleic Acid Hybridization By Nonradiative Fluorescence Resonance Energy Transfer," P.N.A.S. (U.S.A.) 85: 8790–8794 (1988).

A. Coghlan, "Brilliant Beacons Colour–Code Genes," New Scientist p. 24 (Mar. 16, 1996).

B.A. Connolly, et al., "Chemical Synthesis Of Oligonucleotides Containing A Free Sulphydryl Group And Subsequent Attachment Of Thiol Specific Probes," Nucleic Acids Research 13: 4485–4502.

J.P. Cooper, et al., "Analysis Of Fluorescence Energy Transfer In Duplex And Branched DNA Molecules," Biochemistry 29: 9261–9268 (1990).

M.E. DePecol, et al., "Syntheses, Properties, And Use Of Fluorescent N–(5'–Phospho–4'–Pyridoxyl) Amines In Assay Of Pyridoxamine (Pyridoxine) 5'–Phosphate Oxidase," Analytical Biochemistry 101: 435–441 (1980).

H.A. Erlich, et al., "Recent Advances In The Polymerase Chain Reaction," Science 252: 1643–1651 (1991).

D. Gillespie, et al., "A Quantitative Assay For DNA–RNA Hybrids With DNA Immobilized On A Membrane," J. Mol. Biol. 12: 829–842 (1965).

Z. Guo, et al., "Enhanced Discrimination Of Single Nucleotide Polymorphisms By Artificial Mismatch Hybridization," Nature Biotechnology 15: 331–335 (1997).

R.P. Haugland, et al., "Dependence Of The Kinetics Of Singlet–Singlet Energy Transfer On Spectral Overlap," P.N.A.S. (U.S.A.) 63: 23–30 (1969).

P.M. Holland, et al., "Detection Of Specific Polymerase Chain Reaction Product By Utilizing the 5'–3'Exonuclease Activity Of Thermus Aquaticus DNA Polymerase," P.N.A.S. (U.S.A.) 88: 7276–7280 (1991).

P.M. Holland, et al., "Detection Of Specific Polymerase Chain Reaction Product By Utilizing the 5'–3'Exonuclease Activity Of Thermus Aquaticus DNA Polymerase," Clinical Chemistry 38: 462–463 (1992).

E.N. Hudson, et al., "Synthesis And Characterization Of Two Fluorescent Sulfhydryl Reagents," Biochemistry 12: 4154–4161 (1973).

V.M. Ingram, "Gene Mutations In Human Haemoglobin: The Chemical Difference Between Normal And Sickle Cell Haemoglobin," Nature 180: 326–328 (1957).

U. Landegren, et al., "A Ligase–Mediated Gene Detection Technique," Science 241: 1077–1080 (1988).

R. Lathe, "Synthetic Oligonucleotide Probes Deduced From Amino Acid Sequence Data, Theoretical And Practical Considerations," J. Mol. Biol. 183: 1–12 (1985).

L.G. Lee, et al., "Allelic Discrimination By Nick–Translation PCR With Fluorogenic Probes," Nucleic Acid Research 21: 3761–3766 (1993).

P. Lichter, et al., "High–Resolution Mapping Of Human Chromosome 11 By In Situ Hybridization With Cosmid Clones," Science 247: 64–69 (1990).

K.J. Livak, et al., "Towards Fully Automated Genome–Wide Polymorphism Screening," Nature Genetics 9: 341–342 (1995).

H. Lomell, et al., "Quantitative Assays Based On The Use Of Replicatable Hybridization Probes," Clinical Chemistry 35: 1826–1831 (1989).

E.D. Matayoshi, et al., "Novel Fluorogenic Substrates For Assaying Retroviral Proteases By Resonance Energy Transfer," Science 247: 954–958 (1990).

J.A. Matthews, et al., "Analytical Strategies For The Use Of DNA Probes," Analytical Biochemistry 169: 1–25 (1988).

L.E. Morrison, et al., "Sensitive Fluorescence–Based Thermodynamic And Kinetic Measurements Of DNA Hybridization In Solution," Biochemistry 32: 3095–3104 (1993).

L.E. Morrison, et al., "Solution–Phase Detection Of Polynucleotides Using Interacting Fluorescent Labels And Competitive Hybridization," Analytical Biochemistry 183: 231–244 (1989).

N.C. Nelson, et al., "Detection Of All Single–Base Mismatches In Solution By Chemiluminescence," Nucleic Acid Research 24: 4998–5003 (1996).

P.S. Nelson, et al., "Bifunctional Oligonucleotide Probes Synthesized Using A Novel CPG Support Are Able To Detect Single Base Pair Mutations," Nucleic Acids Research 17: 7187–7194 (1989).

Newton, et al., Analysis Of Any Point Mutation In DNA. The Amplification Refractory Mutation System (ARMS) Nucleic Acids Research 17: 2503–2516 (1989).

M. Orita, et al., "Detection Of Polymorphisms Of Human DNA By Gel Electrophoresis As Single–Strand Conformation Polymorphism" P.N.A.S. (U.S.A.) 86: 2766–2770 (1989).

H. Orum, et al., "Single Base Pair Mutation Analysis By PNA Directed PCR Clamping," Nucleic Acids Research 21: 5332–5336 (1993).

K.M. Parkhurst, et al., "Kinetic Studies Of Oligonucleotide–DNA Hybridization In Solution By Fluorescence Resonance Energy Transfer," 37th Ann. Meeting of the Biophysical Society, Washington, D.C., Abstract W–Pos97.

R.K. Saiki, et al., "Genetic Analysis Of Amplified DNA With Immobilized Sequence–Specific Oligonucleotide Probes," P.N.A.S. (U.S.A.) 86: 6230–6234 (1989).

Sambrook, et al., "Molecular Cloning: A Laboratory Manual," Synthetic Oligonucleotide Probes 11.47 and 11.55–11.57.

P.R. Selvin, "Fluorescence Resonance Energy Transfer," Methods in Enzymology 246: 300–335 (1995).

D. Shore, et al., "DNA Flexibility Studied By Covalent Closure Of Short Fragments Into Circles," P.N.A.S. (U.S.A.) 78: 4833–4837 (1981).

S. Sixou, et al., "Intracellular Oligonucleotide Hybridization Detected By Fluorescence Resonance Energy Transfer (FRET)," 37th Ann. Meeting of the Biophysical Society, Washington, D.C., Abstract Tu–Pos351.

S. Sixou, et al., "Intracellular Oligonucleotide Hybridization Detected By Fluorescence Resonance Energy Transfer," Nucleic Acids Research 22: 662–668 (1994).

L. Stryer, "Fluorescence Energy Transfer As A Spectroscopic Ruler," Ann. Rev. Biochem. 47: 819–846 (1978).

N. Tibanyenda, et al., The Effect Of Single Base–Pair Mismatches On The Duplex Stability of d(T–A–T––T–A–A–T–A–T–C–A–A–G–T–T–G) • d(C–A–A–C–T––T–G–A–T–A–T–T–A–A–T–A), Eur. J. Biochem. 139: 19–27 (1984).

S. Tyagi, et al., Molecular Beacons: Probes That Fluoresce Upon Hybridization, Nature Biotechnology 14: 303–308 (1996).

E.F. Ullman, et al., "Fluorescent Excitation Transfer Immunoassay," The Journal of Biological Chemistry 251: 4172–4178 (1976).

G.T. Walker, et al., Strand Displacement Amplification—An Isothermal, In Vitro DNA Amplification Technique Nucleic Acids Research 20: 1691–1696 (1992).

G.T. Wang, et al., "Design And Synthesis Of New Fluorogenic HIV Protease Substrates Based On Resonanc Energy Transfer," Tetrahedron Letters 31: 6493–6496 (1990).

H. Werntges, et al., "Mismatches In DNA Double Strands: Thermodynamic Parameters And Their Correlation To Repair Efficiencies," Nucleic Acids Reseach 14: 3773–3790 (1986).

S.J. Wood, "DNA–DNA Hybridization In Real Time Using BIAcore," Microchemical Journal 47: 330–337 (1993).

C. Yang, et al., Studies Of Transfer RNA Tertiary Sructure By Singlet–Singlet Energy Transfer, P.N.A.S. (U.S.A.) 71: 2838–2842 (1974).

R. Youil, et al., Screening For Mutations By Enzyme Mismatch Cleavage With T4 Endonuclease VII P.N.A.S. (U.S.A.) 92: 87–91 (1995).

FLUORESCEIN

ERYTHROSINE

BODIPY

EOSINE

LUCIFER YELLOW

TETRAMETHLYRHODAMINE

EDANS

TEXAS RED

DABCYL

DABMI

MALACHITE GREEN

COUMARIN

SEQUENCE LISTING

<160> NUMBER OF SEQ ID NOS: 10

<210> SEQ ID NO 1
<211> LENGTH: 16
<212> TYPE: DNA
<213> ORGANISM: Artificial Sequence
<220> FEATURE:
<223> OTHER INFORMATION: synthetically generated

<400> SEQUENCE: 1
aagttaagac ctatga                                                    16

<210> SEQ ID NO 2
<211> LENGTH: 44
<212> TYPE: DNA
<213> ORGANISM: Artificial Sequence
<220> FEATURE:
<223> OTHER INFORMATION: synthetically generated

<400> SEQUENCE: 2
ccgagaaaga aatatcatt ggtgtttcct atgatgaatc tcgg                      44

<210> SEQ ID NO 3
<211> LENGTH: 27
<212> TYPE: DNA
<213> ORGANISM: Artificial Sequence
<220> FEATURE:
<223> OTHER INFORMATION: synthetically generated

<400> SEQUENCE: 3
gcgagccacc aaatatgata tgctcgc                                        27

```
<210> SEQ ID NO 4
<211> LENGTH: 27
<212> TYPE: DNA
<213> ORGANISM: Artificial Sequence
<220> FEATURE:
<223> OTHER INFORMATION: synthetically generated

<400> SEQUENCE: 4
gcgagccacc aaacatgata tgctcgc                                      27

<210> SEQ ID NO 5
<211> LENGTH: 27
<212> TYPE: DNA
<213> ORGANISM: Artificial Sequence
<220> FEATURE:
<223> OTHER INFORMATION: synthetically generated

<400> SEQUENCE: 5
gcgagccacc aaaaatgata tgctcgc                                      27

<210> SEQ ID NO 6
<211> LENGTH: 27
<212> TYPE: DNA
<213> ORGANISM: Artificial Sequence
<220> FEATURE:
<223> OTHER INFORMATION: synthetically generated

<400> SEQUENCE: 6
gcgagccacc aaagatgata tgctcgc                                      27

<210> SEQ ID NO 7
<211> LENGTH: 30
<212> TYPE: DNA
<213> ORGANISM: Artificial Sequence
<220> FEATURE:
<223> OTHER INFORMATION: synthetically generated

<400> SEQUENCE: 7
aaagaaaata tcatatttgg tgtttcctat                                   30

<210> SEQ ID NO 8
<211> LENGTH: 30
<212> TYPE: DNA
<213> ORGANISM: Artificial Sequence
<220> FEATURE:
<223> OTHER INFORMATION: synthetically generated

<400> SEQUENCE: 8
aaagaaaata tcatgtttgg tgtttcctat                                   30

<210> SEQ ID NO 9
<211> LENGTH: 30
<212> TYPE: DNA
<213> ORGANISM: Artificial Sequence
<220> FEATURE:
<223> OTHER INFORMATION: synthetically generated

<400> SEQUENCE: 9
aaagaaaata tcatttttgg tgtttcctat                                   30

<210> SEQ ID NO 10
<211> LENGTH: 30
<212> TYPE: DNA
```

-continued

```
<213> ORGANISM: Artificial Sequence
<220> FEATURE:
<223> OTHER INFORMATION: synthetically generated

<400> SEQUENCE: 10
aaagaaaata tcatctttgg tgtttcctat                                      30
```

NUCLEIC ACID DETECTION PROBES HAVING NON-FRET FLUORESCENCE QUENCHING AND KITS AND ASSAYS INCLUDING SUCH PROBES

This application is a continuation of application PCT/US97/06208, filed Apr. 14, 1997, which is a continuation-in-part of application PCT/US97/06532, filed Apr. 12, 1997, both of which claim priority of U.S. provisional application 60/015,409, filed Apr. 12, 1996.

This invention was in part made with government support under grant number HL-43521-07, awarded by the National Institutes of Health. The United States government has certain rights in that part of the invention.

This invention relates to nucleic acid hybridization probes containing fluorophore and chromophore labels, and kits and assays containing and employing them.

BACKGROUND

There are many different types of assays that employ nucleic acid hybridization probes and that utilize for signal generation a change in the fluorescence of a fluorophore due to a change in its interaction with another molecule or moiety brought about by changing the distance between the fluorophore and the interacting molecule or moiety.

These assays rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore. Stryer, L., "Fluorescence Energy Transfer as a Spectroscopic Ruler," Ann. Rev. Biochem. 1978, 47: 819–846 ("Stryer, L. 1978"); BIOPHYSICAL CHEMISTRY part II, Techniques for the Study of Biological Structure and Function, C. R. Cantor and P. R. Schimmel, pages 448–455 (W. H. Freeman and Co., San Francisco, U.S.A., 1980) ("Cantor and Schimmel 1980"), and Selvin, P. R., "Fluorescence Resonance Energy Transfer," Methods in Enzymology 246: 300–335 (1995) ("Selvin, P. R. 1995"). Efficient, or a substantial degree of, FRET interaction requires that the absorption and emission spectra of the pair have a large degree of overlap. The efficiency of FRET interaction is linearly proportional to that overlap. Haugland, R. P., Yguerabide, Jr., and Stryer, L., "Dependence of the Kinetics of Singlet-Singlet Energy Transfer on Spectral Overlap," P.N.A.S. (U.S.A.) 63: 24–30 (1969) ("Haugland et al. 1969"). The cited art teaches that to obtain a large magnitude of signal, a high degree of overlap is required. FRET pairs, including fluorophore-quencher pairs, have been chosen on that basis.

One suitable FRET pair disclosed in Matayoshi et al. 1990, Science 247: 954–958, includes DABCYL as a quenching moiety (or quenching label) and EDANS as a fluorophore (or fluorescent label). The absorption spectrum of DABCYL has a high degree of overlap with the emission spectrum of EDANS, making these two a good FRET pair. Despite the recognized advantage of using a FRET pair that includes a quencher that does not itself fluoresce, such as DABCYL, very few such FRET pairs have been identified. In general, the number of fluorophore-quencher pairs is extremely limited because of the need for a high degree of spectral overlap. Additional such pairs would be highly desirable for a number of reasons, including flexibility in assay design and distinguishing signals in multiplex assays.

A variety of labeled nucleic acid hybridization probes and detection assays that utilize FRET and FRET pairs are known. One such scheme is described by Cardullo et al. (1988), P.N.A.S. 85: 8790–8794 and in Heller et al. EP 0070685. A2, claiming priority of U.S. 284469 filed on Jul. 17, 1981. It uses a probe comprising a pair of oligodeoxynucleotides complementary to contiguous regions of a target DNA strand. One probe molecule contains a fluorescent label, a fluorophore, on its 5' end, and the other probe molecule contains a different fluorescent label, also a fluorophore, on its 3' end. When the probe is hybridized to the target sequence, the two labels are brought very close to each other. When the sample is stimulated by light of an appropriate frequency, fluorescence resonance energy transfer from one label to the other occurs. FRET produces a measurable change in spectral response from the labels, signaling the presence of targets. One label could be a "quencher," which in this application is meant an interactive moiety (or molecule) that releases the accepted energy as heat.

Another solution-phase scheme utilizes a probe comprising a pair of oligodeoxynucleotides and a FRET pair. However, here the two probe molecules are completely complementary both to each other and to complementary strands of a target DNA (Morrison and Stols, "Sensitive Fluorescence-Based Thermodynamic and Kinetic Measurements of DNA Hybridization in Solution,"Biochemistry 32: 309–3104 (1993) and Morrison EP 0 232 967 A2, claiming priority of U.S. application Ser. No. 817,841, filed Jan. 10, 1986. Each probe molecule includes a fluorophore conjugated to its 3' end and a quenching moiety conjugated to its 5' end. When the two oligonucleotide probe molecules are annealed to each other, the fluorophore of each is held in close proximity to the quenching moiety of the other. With the probe in this conformation, if the fluorophore is then stimulated by light of an appropriate wavelength, the fluorescence is quenched by the quenching moiety. However, when either probe molecule is bound to a target, the quenching effect of the complementary probe molecule is absent. In this conformation a signal is generated. The probe molecules are too long to self-quench by FRET when in the target-bound conformation.

A solution-phase scheme that utilizes FRET pairs and the phenomenon known as strand displacement is described by Diamond et al. U.S. Pat. No. 4,766,062; Collins et al. U.S. Pat. No. 4,752,566; Fritsch et al. U.S. Pat. Nos. 4,725,536 and 4,725,537. Typically, these assays involve a probe comprising a bimolecular nucleic acid complex. A shorter single strand comprising a subset of the target sequence is annealed to a longer single strand which comprises the entire target binding region of the probe. The probe in this configuration thus comprises both single-stranded and double-stranded portions. Diamond et al. proposed that these probes may further comprise either a $^{32}P$ label attached to the shorter strand or a fluorophore and a quencher moiety which could be held in proximity to each other when the probe conformation is that complex.

Another type of molecular probe assay utilizing a FRET pair is described in European Patent Application 0 601 889 A3, publication date Jun. 15, 1994, which claims priority of Bagwell U.S. patent application Ser. No. 990,298, filed Dec. 10, 1992.

Another type of nucleic acid hybridization probe assay utilizing a FRET pair is the so-called "TaqMan" assay described in Gelfand et al. U.S. Pat. No. 5,210,015, and Livak et al. U.S. Pat. No. 5,538,848. The probe is a single-stranded oligonucleotide labeled with a FRET pair. In a "TaqMan" assay, a DNA polymerase releases single or multiple nucleotides by cleavage of the oligonucleotide probe when it is hybridized to a target strand. That release provides a way to separate the quencher label and the fluorophore label of the FRET pair. According to Livak et al. "straightening" of an end-labelled "TaqMan" probe also reduces quenching.

Yet another type of nucleic acid hybridization probe assay utilizing FRET pairs is described in Tyagi et al. copending United States patent application Ser. No. 08/439,819 now U.S. Pat. No. 5,925,517 (and counterpart applications outside the United States, including PCT Application No. WO 95/13399), which utilizes labeled oligonucleotide probes, which we have come to refer to as "Molecular Beacons." Tyagi, S. and Kramer, F. R., "Molecular Beacons: Probes that Fluoresce upon Hybridization," Nature Biotechnology 14: 303–308 (1996). A Molecular beacon probe is an oligonucleotide whose end regions hybridize with one another in the absence of target but are separated if the central portion of the probe hybridizes to its target sequence. The rigidity of the probe-target hybrid precludes the simultaneous existence of both the probe-target hybrid and the intramolecular hybrid formed by the end regions. Consequently, the probe undergoes a conformational change in which the smaller hybrid formed by the end regions disassociates, and the end regions are separated from each other by the rigid probe-target hybrid.

Aspects of this invention include probes containing non-FRET fluorophore-quencher pairs and chromophore pairs useful in assays; improved assays, including multiplexed assays, utilizing such pairs of molecules or moieties; and assay kits that include such pairs.

SUMMARY OF THE INVENTION

As opposed to FRET, quenching molecules and even other fluorophores can serve as efficient quenching moieties for fluorophores when attached to nucleic acid hybridization probes such that the fluorescing moiety and quenching moiety are in contact, even when the rules of FRET are violated. Further, the absorption spectra of a pair of chromophores (fluorescing or non-fluorescing), even identical chromophores, in a probe so constructed is altered in a detectable fashion.

In FRET, a first fluorophore absorbs at a first wavelength and emits at a second, longer wavelength. A second fluorophore or quencher which is near the first (the FRET range is reportedly 10–100 Å), if and to the degree its absorption spectrum overlaps that emission, absorbs some or most of the emitted energy and, if a fluorophore, re-emits at a third, still longer wavelength, or, if a quencher, releases the energy as heat. FRET progresses in the direction of increasing wavelength. It does not progress in the direction of decreasing wavelength. A probe according to this invention is a "nucleic acid hybridization probe," which as used herein means a probe that is hybridizable to a natural oligonucleotide strand and is composed of natural or modified nucleotides joined by natural or non-natural linkages. A peptide nucleic acid probe is a "nucleic acid hybridization probe," as are, of course, DNA probes, RNA probes and probes of mixed DNA and RNA. The term "probe" as used herein includes a single molecule and also a pair of molecules that in combination affect the level of signal.

A probe according to this invention is capable of undergoing a conformational change upon interacting with a target in an assay. Preferably a pair of labels, for example, a fluorophore and a quencher, "touch" all or part of the time when the probe is not interacting with target, and interaction with target separates the label pair, thereby preventing "touching". Examples of such probes include certain of the following probe constructions: bimolecular probes disclosed in Morrison EP 0 232 967 A2, bimolecular probes disclosed in Diamond et al. U.S. Pat. No. 4,766,062, single-molecule oligonucleotide probes such as disclosed in Gelfand et al. U.S. Pat. No. 5,210,015 and Livak et al. U.S. Pat. No. 5,538,848 ("TaqMan" probes) and self-hybridizing single-molecule probes disclosed in Tyagi et al. U.S. patent application Ser. No. 08/439,819, now U.S. Pat. No. 5,925,517 PCT Application No. WO 95/13399 and Nature Biotechnology 14: 303–308 (1996) ("Molecular Beacon" probes). However, a probe according to this invention may function in the opposite manner such that a label pair is made to "touch" by interaction of the probe with its target. An example of such a probe is the bimolecular probe disclosed in Heller et al. EP 0070685.A2. Our most preferred probe constructions are "Molecular Beacon" probes.

When attached to a probe according to this invention such that it is in contact with, or "touching", the first fluorophore in one of its conformations, a quenching moiety need not have an absorption spectrum that overlaps the emission spectrum of the first fluorophore. Moreover, the absorption wavelength of the quencher can be shorter than the fluorophore's excitation maximum and emission wavelength. Similarly, a second fluorophore that absorbs at a wavelength shorter than the emission wavelength of the first can, in the probe construction described above, act as a quencher; that is, suppress emission by the first fluorophore and dissipate the incident energy as heat rather than as photon emission.

In probes constructed as described above, change in the absorption spectra of the label pair can be used as a detectable signal, as an alternative to change in fluorescence. When change in absorption is utilized, the label pair may include any two chromophores, that is, fluorophores, quenchers and other chromophores. The label pair may even be identical chromophores.

In addition to probes, this invention includes assays employing such probes and assay kits containing them.

DETAILED DESCRIPTION OF THE INVENTION

One type of probe structure useful in this invention is the "Molecular Beacon" oligonucleotide structure described in U.S. patent application Ser. No. 08/439,819(now U.S. Pat. No. 5,925,517), incorporated by reference herein in its entirety, PCT Application No. WO 95/13399, and Tyagi, S. and Kramer, F. R., "Molecular Beacons: Probes that Fluoresce upon Hybridization," Nature Biotechnology 14: 303–308 (1996). In those probes, a central target-recognition sequence is flanked by arms that hybridize to one another when the probe is not hybridized to a target strand, forming a "hairpin" structure, in which the target-recognition sequence (which is commonly referred to as the "probe sequence") is in the single-stranded loop of the hairpin structure, and the arm sequences form a double-stranded stem hybrid. When the probe hybridizes to a target, that is, when the target-recognition sequence hybridizes to a complementary target sequence, a relatively rigid helix is formed, causing the stem hybrid to unwind and forcing the arms apart. A FRET pair, such as the fluorophore EDANS and the quencher DABCYL, may be attached to the arms by alkyl spacers. When the Molecular Beacon is not hybridized to a target strand, the fluorophore's emission is quenched. When the Molecular Beacon is hybridized to a target strand, the FRET pair is separated by more than 100 Å, and the fluorophore's emission is not quenched. Emitted fluorescence signals the presence of target strands. Molecular beacon probes may have target recognition sequences 7–140 nucleotides in length and arms that form a stem hybrid, or "stem duplex" 3–25 nucleotides in length. Modified nucleotides and modified nucleotide linkages may be used. Molecular beacons may be, for example, peptide nucleic acid ("PNA") probes.

Figure 6:
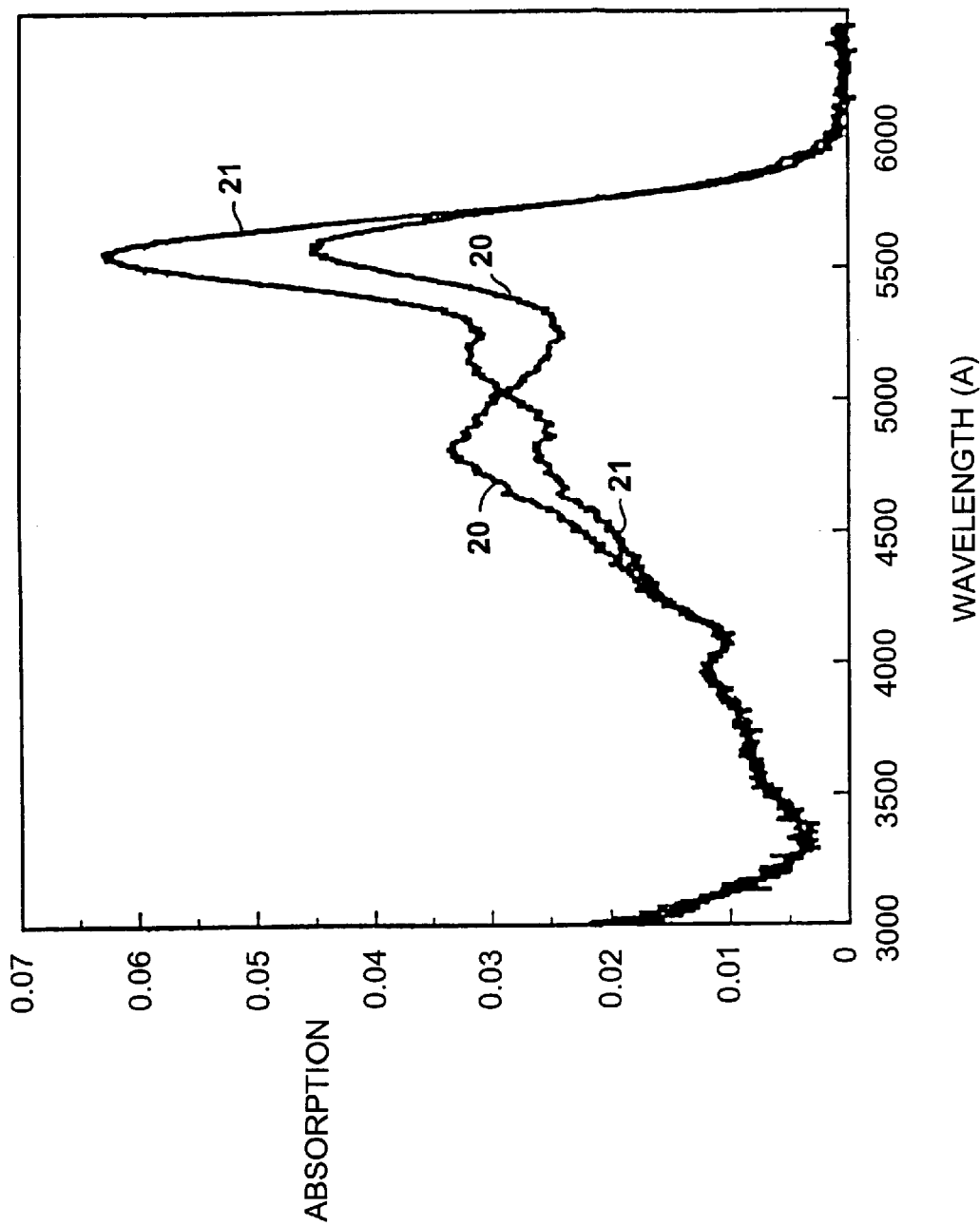
FIG. 6 shows absorption spectra for a pair of chromophores when touching and when separated.
Figure 7B:
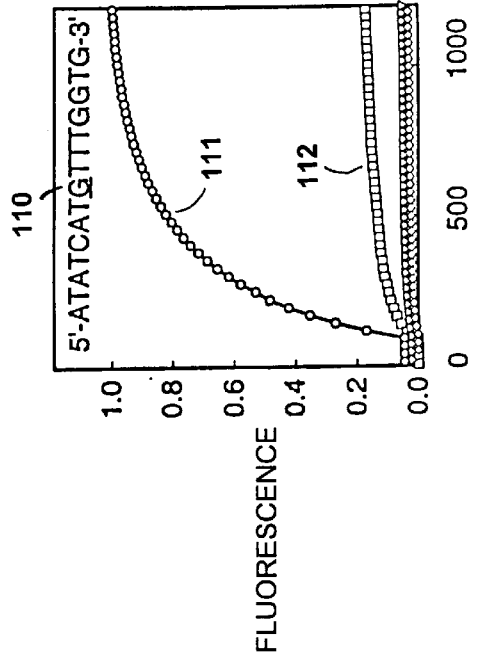
FIGS. 7A–7D shows kinetic fluorescence measurements using four probes in a multiplex assay.
Figure 7D:
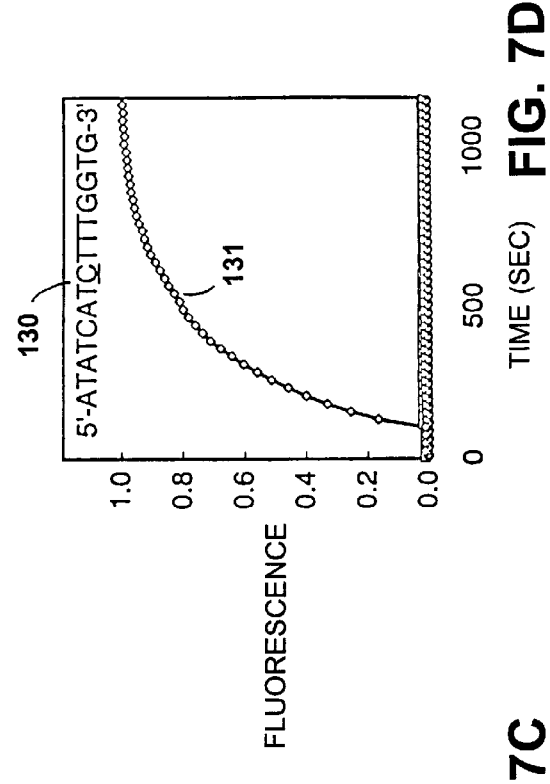
Figure 7A:
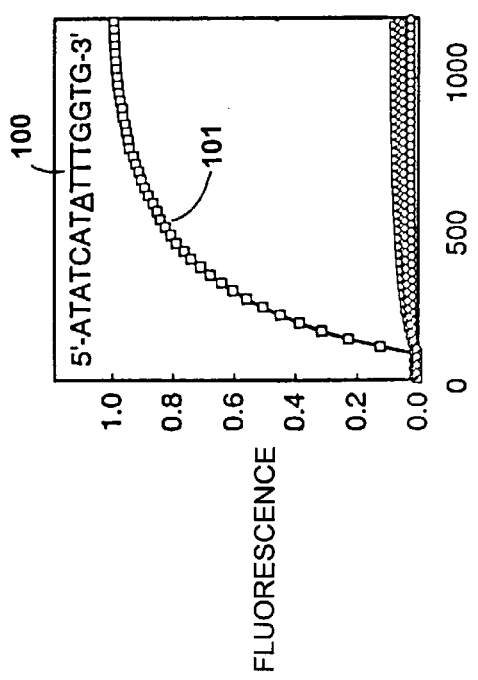
Figure 7C:
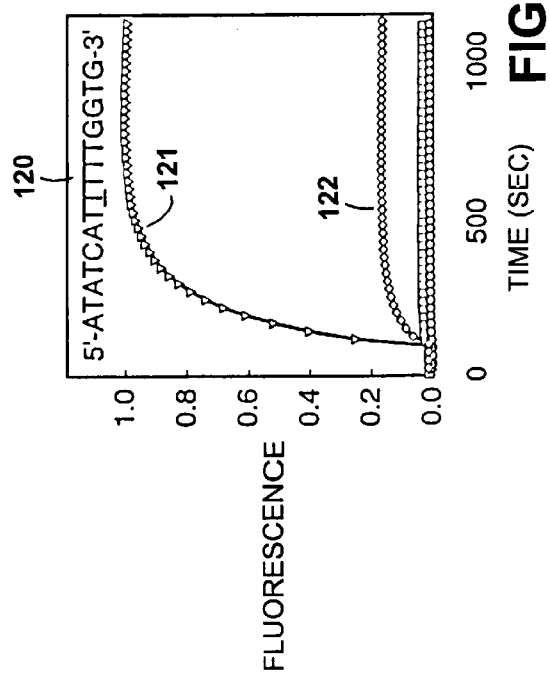

We have discovered that in certain Molecular Beacon probes, a pair of labels "touches" when the probe is not hybridized to a target. By "touching" we mean that the absorption spectrum of the pair is significantly altered. FIG. 6 presents absorption spectra for a Molecular Beacon whose complementary terminal nucleotides are part of a stem hybrid. The probe was labeled with DABCYL on one end and Tetramethylrhodamine on the other end. Spectrum 20 is from the probe in a first conformation, not bound to target, with the arms hybridized to one another. Spectrum 21 is from the probe in a second conformation, bound to target, with the arms not hybridized. The absorption maxima are at about 4800 Å and 5500 Å in spectrum 21. Comparison of spectrum 20 with spectrum 21 shows that the label pair are "touching" when the arms are hybridized: absorption at 4800 Å is reduced from about 0.033 to about 0.026, and absorption at 5500 Å is increased from about 0.046 to about 0.063. FRET would not change the absorption spectrum of the pair. Van Der Meer, B. W., Coker, G., III, and Chen S-Y. S., RESONANCE ENERGY TRANSFER, VCH Publishers, Inc. (New York 1994). Whether or not two chromophores are "touching" can be determined by comparing the absorption spectrum when they are touching to the absorption spectrum when they are separated by more than 100 Å, as shown in FIG. 6.

We have discovered that a quencher, for example DABCYL, attached to one end of a Molecular Beacon constructed as described in the preceding paragraph, will effectively quench fluorophores attached to the other end in violation of FRET rules, thereby greatly enlarging the available number of fluorophore-quencher pairs that can be used in nucleic acid hybridization probes.

Figure 1:
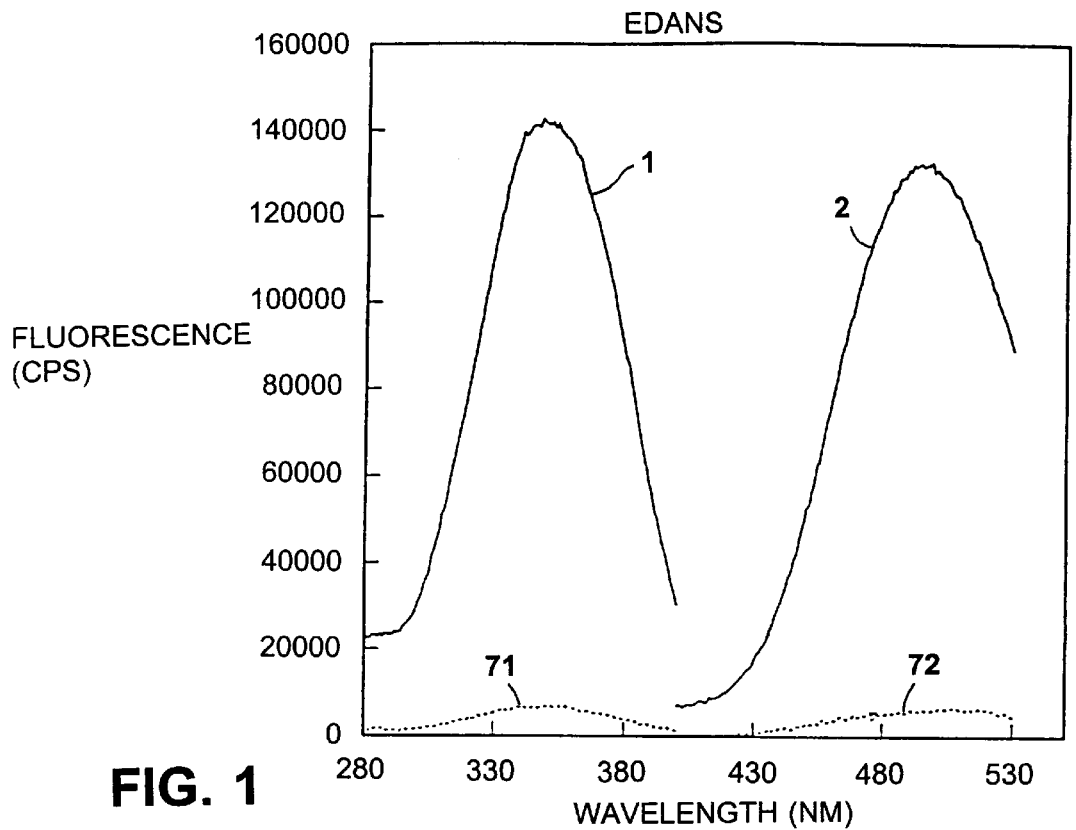
FIG. 1 shows excitation and emission spectra for EDANS-labeled DNA.
Figure 2:
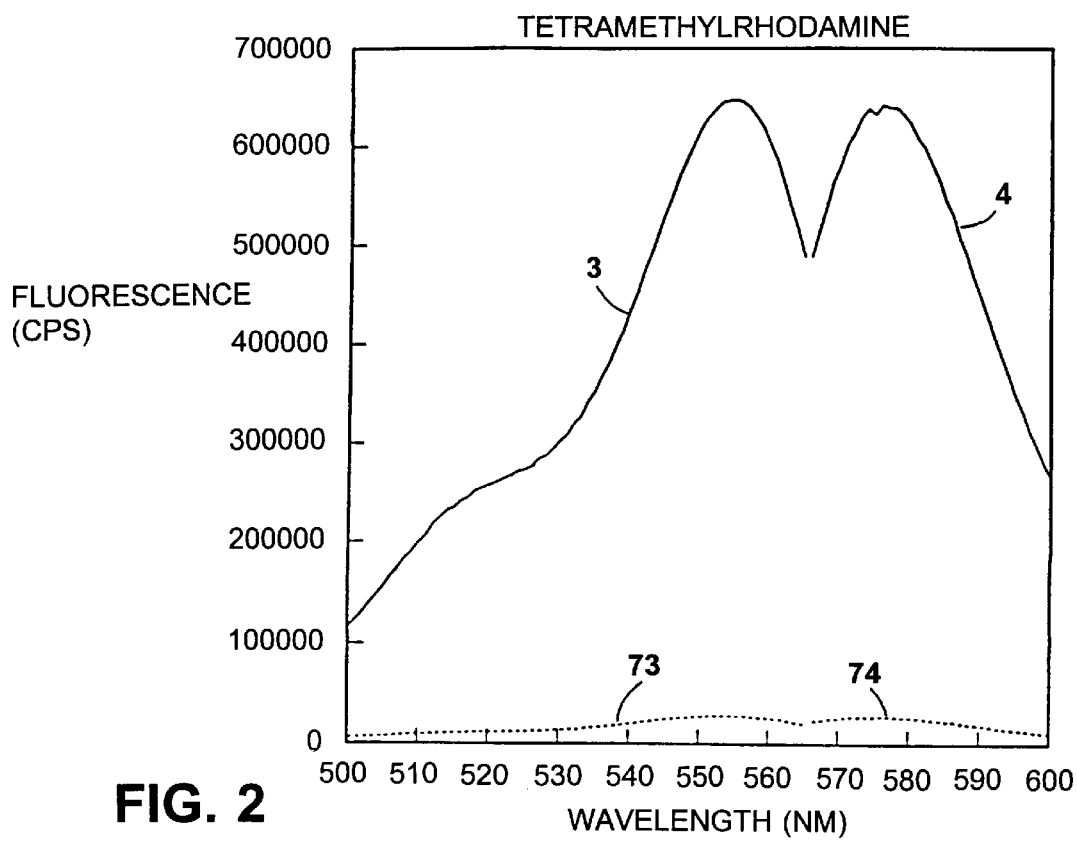
FIG. 2 shows excitation and emission spectra for Tetramethylrhodamine-labeled DNA.
Figure 3:
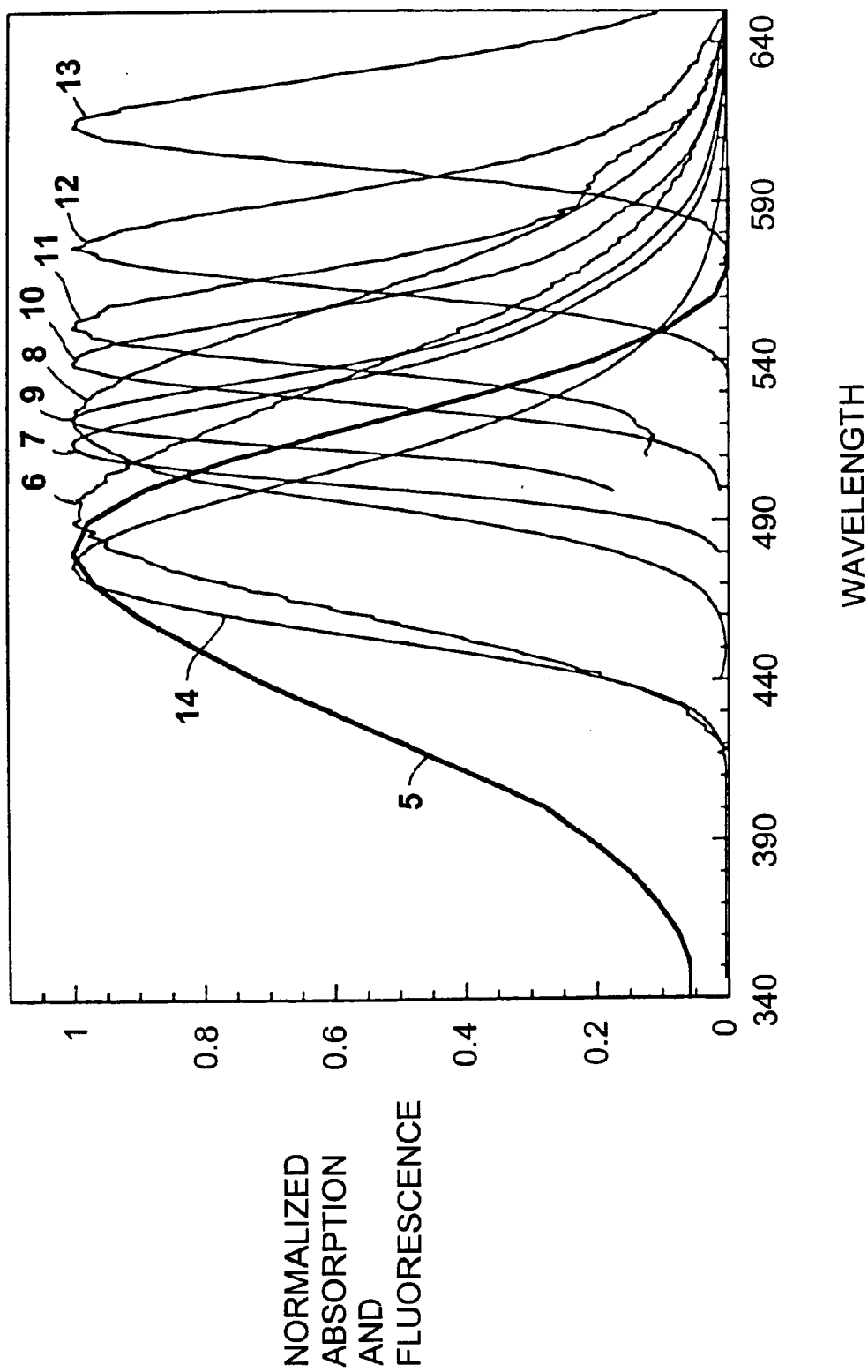
FIG. 3 is a graph showing the absorption spectrum of DABCYL and emission spectra for each of nine fluorophores.

The following description references the spectral data presented in FIGS. 1, 2 and 3. FIG. 1 presents the excitation (curve 1 on the left, shorter wavelength) and emission (curve 2 on the right, longer wavelength) spectra of a Molecular Beacon containing the quencher DABCYL and the fluorophore EDANS, when it is hybridized to a target. FIG. 2 presents the excitation spectrum (curve 3) and emission spectrum (curve 4) of a Molecular Beacon containing the quencher DABCYL and the fluorophore Tetramethylrhodamine, when it is hybridized to a target.

FIG. 3 presents the absorption spectrum 5 for the quencher DABCYL and emission spectra 6–14 for a number of fluorophores: EDANS(6), Fluorescein(7), Lucifer Yellow (8), BODIPY(9), Eosine(10), Erythrosine(11), Tetramethylrhodamine(12), Texas Red(13) and Coumarin (14). The large overlap for EDANS and Coumarin with DABCYL demonstrates why EDANS and DABCYL and Coumarin and DABCYL are FRET pairs. Curve 12 is the emission spectrum for Tetramethylrhodamine. It has almost no overlap with the absorbance spectrum of DABCYL. Curve 13 is the emission spectrum for Texas Red. It has no overlap with the absorbance spectrum of DABCYL. According to FRET rules, the degree of fluorescence energy transfer is a function of the amount of spectral overlap.

Initially using the procedure described in Example 1, we determined the spectral overlap of several fluorophores with an exemplary quencher, for which we chose DABCYL. The calculated overlap and the consequent expected degree of quenching are summarized in Table 1.

TABLE 1

Quenching with DABCYL by FRET

| Fluorophore | Spectral Overlap | Expected FRET Quenching Efficiency, % |
| --- | --- | --- |
| EDANS | 4856 | 95.60 |
| Fluorescein | 1448 | 30.38 |
| Lucifer Yellow | 2485 | 52.15 |
| BODIPY | 1050 | 22.04 |
| Eosine | 409 | 8.58 |
| Erythrosine | 184 | 3.86 |
| Tetramethylrhodamine | 2 | 0.05 |
| Texas Red | 0 | 0.00 |

For use in an assay, a quencher or interacting fluorophore should have sufficient spectral overlap, as spectral overlap was determined by the procedure of Example 1, to absorb at least 60% of a fluorophore's emission by fluorescence resonance energy transfer, which we define as the minimal interaction to be considered a "FRET pair" as that term is used herein. According to that description, only EDANS of the fluorophores in Table 1 forms a FRET pair with the quencher DABCYL. We have discovered, however, that when DABYCL or another suitable quencher contacts or "touches" any of the seven other fluorophores tested, efficient quenching is achieved.

To demonstrate embodiments of probes with "touching" pairs of a fluorophore with another fluorophore or quencher, where the pairs are not FRET pairs as defined above, we prepared Molecular Beacon probes end-labeled with DABCYL at one end and one of eight different fluorophores at the other end. We tested quenching efficiency by the procedures described in Example 2. Table 2 presents the observed quenching efficiency and also the expected quenching efficiency by FRET. FIG. 6 demonstrates that "touching" is achieved, and Table 2 shows the effect on quenching that results for non-FRET pairs, which includes all fluorophores in Table 2 except EDANS.

TABLE 2

Quenching by "Touching"

| Fluorophore | Expected FRET Quenching Efficiency, % | Observed Quenching Efficiency, % |
| --- | --- | --- |
| EDANS | 95.60 | 95.60 |
| Fluorescein | 30.38 | 94.52 |
| Lucifer Yellow | 52.15 | 96.84 |
| BODIPY | 22.04 | 94.17 |
| Eosine | 8.58 | 90.66 |
| Erythrosine | 3.86 | 72.22 |
| Tetramethylrhodamine | 0.05 | 95.77 |
| Texas Red | 0.00 | 99.10 |

Not all Molecular Beacon designs are considered likely candidates for probes according to this invention, because "touching" is required. Only Molecular Beacons having a label pair attached such that the label moieties can touch when the probe is not hybridized to a target may be probes according to this invention. Besides the end-labeling described above, another configuration that should be useful is to separate the label moieties by five nucleotides along the stem hybrid. This brings the two labels to the same side of the helix, because the helix makes a complete turn every ten nucleotides. Separation by four or six nucleotides along the helix would be less preferred candidates. To ascertain whether or not a particular Molecular Beacon design is suitable for probes according to this invention, one can simply prepare a probe and test it by the procedures described herein.

The same applies to other probe constructions. The data presented here establishes that probe pairs of the types described in Heller et al. EP 0070685.A2, Morrison EP 0232967.A2 and Diamond U.S. Pat. No. 4,766,062 will provide "touching" if the two molecules of the probe are end-labeled in the fashion described herein for Molecular Beacons. Other candidate configurations should be tested.

Probes according to this invention include probes whose labels can "touch", but in fact "touch" only part of the time, such as, for example, a "TaqMan" probe or other single-stranded probe that is labeled along the probe. Such linear probes form a random coil when not hybridized. Probes that "touch" only part of the time will tend to be less efficiently quenched and generate higher background than probes such as the preferred Molecular Beacon probes described herein and are, therefore, less preferred. To be useful in this invention such a probe must provide at least 20% quenching, preferably 25% or even 30% and more preferably at least 40% quenching, according to the procedure of Example 2.

To demonstrate probes whose labels "touch" only part of the time, we prepared three non-self-hybridizing oligonucleotide probes. They were thirteen nucleotides long and end-labeled with DABCYL (3' end) and one of three fluorophores—EDANS, Fluorescein or Tetramethyl-rhodamine (5' end). We hybridized the three probes to an unlabeled, perfectly complementary target oligonucleotide, of the same length as the probes and we hybridized the three probes to a perfectly matched target oligonucleotide labeled at its 3' end with DABCYL. The first target eliminates quenching, and the second target maximizes quenching by "touching" the fluorophore to the target's DABCYL moiety. Utilizing the procedure of Example 2, we measured quenching efficiency when the probes were not hybridized (a random-coil state) and hybridized to each target. Table 3 presents those results.

TABLE 3

Observed Quenching Efficiency, %

| Probe/State | fluorophore paired with DABCYL | | |
| --- | --- | --- | --- |
| | EDANS | Fluorescein | Tetramethylrhodamine |
| 13-mer/unhybridized | 76 | 81 | 44 |
| 13-mer/hybridized to unlabeled target | 0 | 0 | 0 |
| 13-mer/hybridized to labeled target | 96 | 95 | 96 |

The results in Table 3 show that for a probe according to this invention in which the label pair (Tetramethylrhodamine-DABCYL) has essentially no spectral overlap, precluding FRET interaction completely, nearly half of the fluorescence (44%) was quenched by "touching" part of the time due to random-coil movement. A probe according to this invention in which the label pair (Fluorescein-DABCYL) has some spectral overlap but not enough to be a FRET pair was quenched as well as the probe with the FRET pair (EDANS-DABCYL). The background from all three 13-mer oligonucleotide probes was shown to be considerably higher than from similarly labeled Molecular Beacon probes, which give better quenching and, thus, higher signal-to-background ratios.

To be useful in this invention, a non-FRET fluorophore-quencher pair when attached to complementary ends of a hybrid must satisfy certain criteria when tested according to Examples 1 and 2 presented below. The pair must yield a degree of quenching above 60 percent, preferably at least 70 percent and more preferably at least 80% to minimize background signal. In addition, the quenching efficiency must be at least 10 percent greater than predicted by spectral overlap, which follows from the significant change in absorbance that signifies "touching". Preferably, the quenching efficiency is at least 30 percent greater than predicted by spectral overlap.

A quencher suitable for use in this invention should satisfy several criteria. First, it is a chromophore that is not a fluorophore; it can absorb light and dissipate energy as heat. Second, it should be a relatively good absorber; it preferably should have an extinction coefficient of at least $10^4$ $M^{-1}$. Third, it should not repel or seek to avoid the fluorophore to be quenched; that is, if the fluorophore is hydrophobic, the quencher should also be hydrophobic, and if the fluorophore is positively or negatively charged, the quencher should not be similarly charged. Fourth, it should not be chemically reactive in use, particularly it should not generate destructive free radicals. Finally, for ease of use, it should be available in an activated form containing leaving groups for coupling to the probe. Quenchers satisfying these criteria include, for example, DABCYL, DABMI and Malachite Green, all of which appear in FIG. 5.

A second fluorophore that does not form a FRET pair with the first fluorophore can be used in place of a quencher. Preferably the second fluorophore has no spectral overlap or minimal spectral overlap with the first fluorophore. Criteria for selecting a second fluorophore are basically the same as for selecting a quencher. Considering the first fluorophore to be the one excited in an assay, it is preferred that the excitation spectrum of the second fluorophore be at wavelengths shorter, completely or nearly so, than the emission excitation spectrum of the first fluorophore. Coumarin, a fluorophore that normally emits in the blue range, has been shown to act as a quencher for Tetramethylrhodamine in a Molecular Beacon probe according to this invention.

Although change in fluorescence is preferred for detection in this invention, "touching" permits change in absorbance to be used for detection. As explained above in connection with FIG. 6, the absorption spectrum changes when two chromophores, fluorescing or non-fluorescing, are made to "touch". We have shown this occurs, utilizing a Molecular Beacon labeled at both ends with Tetramethylrhodamine. Other label pairs could be, for example, the non-fluorophores DABCYL-DABCYL, Malachite Green-DABCYL or Malachite Green-Malachite Green, or the fluorophores Fluorescein-Tetramethylrhodamine. FIG. 6 demonstrates that the label pair could be DABCYL-Tetramethylrhodamine. For use with absorption detection, one could select a suitable pair by obtaining absorption spectra for the probe in the "touching" and "non-touching" configurations, and ascertaining if the change in absorption is a suitable signal for the test or assay and the sensitivity of the instrument to be used. Where two different chromophores are used, the change in the ratio of absorptions at their peak wavelengths is a convenient way to measure signal change. Preferably, where absorbance is used for detection, the labels should have extinction coefficients of at least $3 \times 10^4$ $M^{-1}$.

Attachment of chromophores to the probe is by conventional means. The points of attachment, taking into consideration linkers, such as alkyl spacers, for example, must permit the two labels to "touch" as defined above. Complementary end nucleotides of a hybrid (whether in one or separate molecules) ensure "touching", as demonstrated by the Molecular Beacons described herein.

This invention also includes assays that utilize chromophore pairs, preferably fluorescer-quencher pairs, of this invention. Thus, in an assay that relies for generation of a signal on quenching the fluorescence of a fluorophore, this invention includes the improvement comprising using a fluorophore-quencher pair wherein the quencher is, for example, DABCYL and the degree of quenching is at least 60%, preferably 70% and more preferably 80%, and at least 10%, preferably at least 30%, above the quenching efficiency expected based on spectral overlap. An assay according to this invention can be a multiplex assay that includes multiple fluorescer-quencher pairs and generates multiple signals. The assays may be detection assays, either qualitative, quantitative or both. Detection may comprise part of a larger process that includes, for example, a nucleic acid amplification. This will be the case particularly if detection is in real-time during the amplification or other process. Well-known amplification processes include the polymerization chain reaction ("PCR") process disclosed, for example, in U.S. Pat. Nos. 4,683,202, 4,683,195 and 4,965,188; Q-beta replication (Lomeli et al., "Quantitative Assays Based on the Use of Replicable Hybridization Probes," Clin. Chem. 39, 1826–1831 (1989)); NASBA; self-sustained sequence reactions ("3SR") (Guatelli et al., "Isothermal in vitro Amplification of Nucleic Acids by Multienzyme Reaction Modeled after Retroviral Replication," P.N.A.S. (U.S.A.) 87: 1874–1878 (1990)) and transcription and replication reactions.

Our invention also includes reagent kits that include labeled probes according to this invention, together with other reagents for an assay. For example, a kit may include enzymes, primers and buffers for a PCR reaction together with Molecular Beacons for detecting amplified product. For multiplex assays, kits according to this invention will include multiple probes, at least one of which is a probe according to this invention. For example, several Molecular Beacons can be included, each labeled according to this invention with DABCYL as a quencher, but each with a different fluorophore. In that case at least one probe will include a non-FRET fluorophore-quencher pair according to this invention. Another pair may be a recognized FRET pair, such as EDANS and DABCYL. Multiple probes according to this invention may, of course, be included. For multiplexing with fluorescence detection, it will be recognized that it is desirable to minimize the overlap of both the excitation spectra and the emission spectra of the different fluorophores. For multiplexing with absorption detection, it will be recognized that it is desirable to minimize the overlap of absorption spectra of the different probes.

Figure 4:
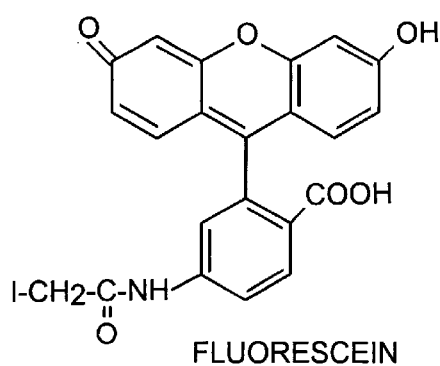
FIG. 4 shows the chemical structure of reactive forms of a number of fluorophores.
Figure 4:
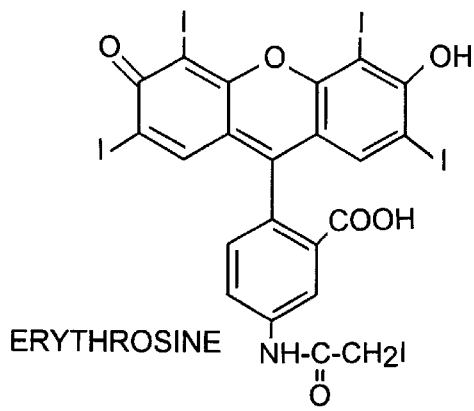
Figure 4:
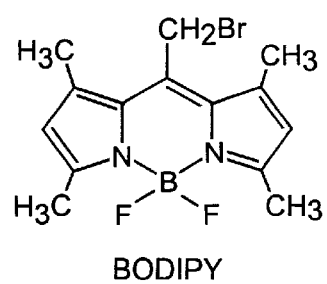
Figure 4:
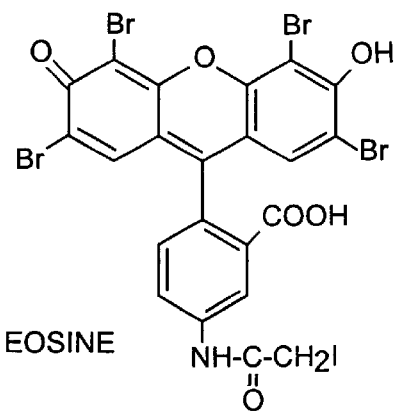
Figure 4:
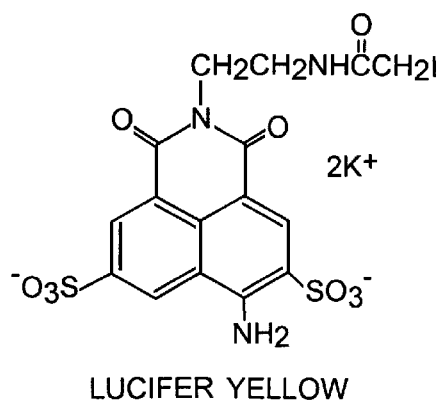
Figure 4:
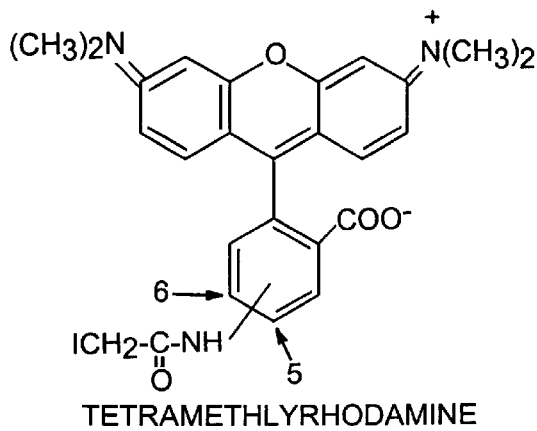
Figure 4:
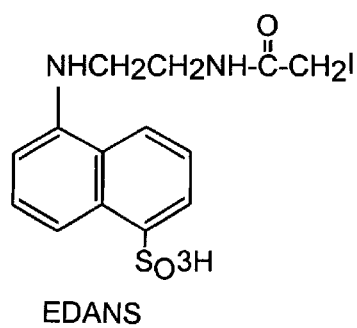
Figure 4:
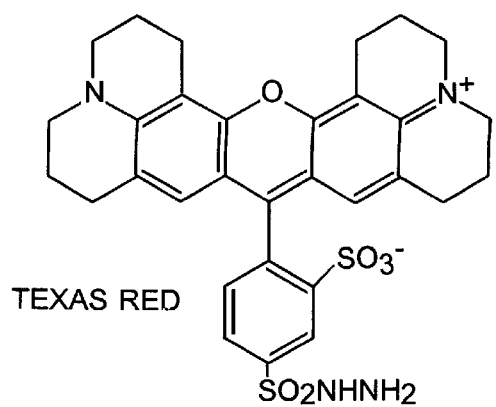
Figure 5:
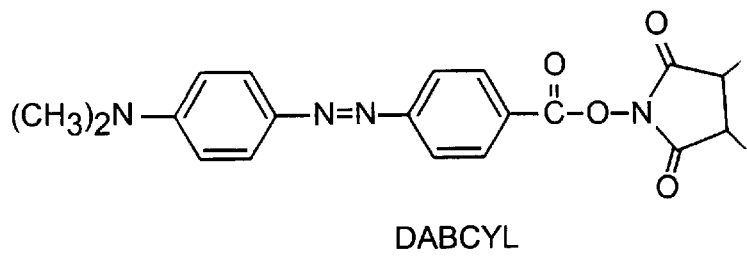
FIG. 5 shows the chemical structures of reactive forms of several quenchers and a fluorophore used as a quencher.
Figure 5:
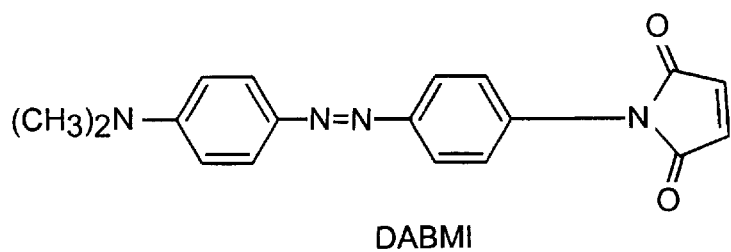
Figure 5:
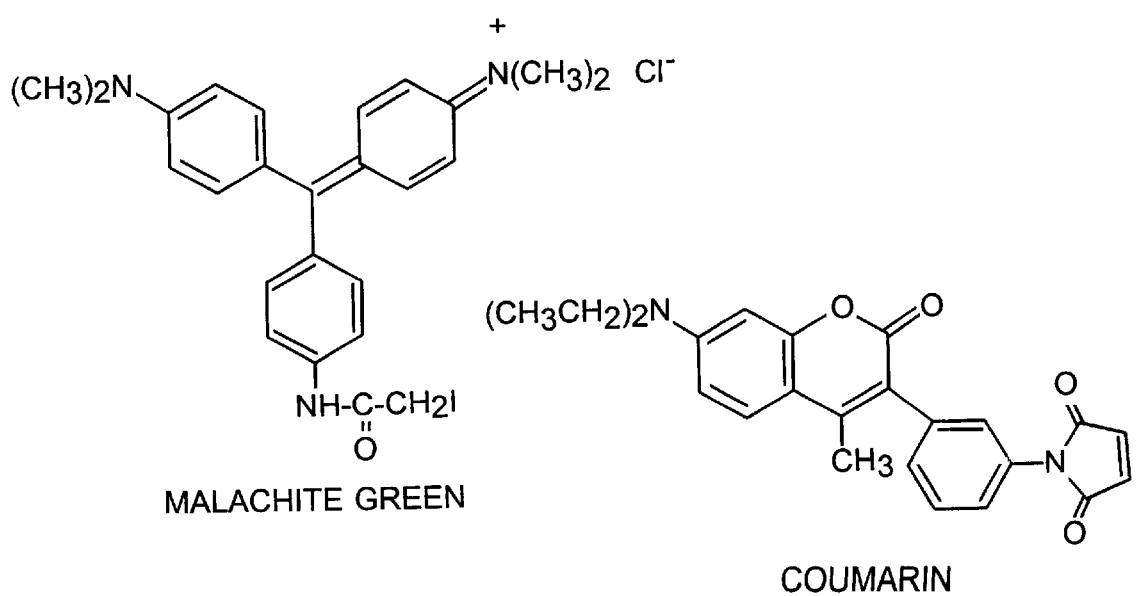

Using the assay procedures described herein, we have shown that DABCYL can quench the fluorescence of Fluorescein, Lucifer Yellow, BODIPY, Eosine, Erythrosine, Tetramethylrhodamine, Texas Red and Coumarin, all commercially available fluorophores whose chemical structures are well known and published. We have also shown effective fluorophore quenching in non-FRET pairs containing other quenchers, DABMI and Malachite Green, as well as appropriate (shorter wavelength) fluorophores such as Coumarin. FIG. 4 shows the chemical structures of the reactive forms of fluorophores, and FIG. 5 shows the chemical structures of the reactive forms of Coumarin, DABMI, Malachite Green and DABCYL, as reported in the catalog of Molecular Probes, Inc., Eugene, Oregon, U.S.A., entitled "Handbook of Fluorescent Probes and Research Chemicals," 5th Ed. 1992–1994, by R. P. Haugland (K. D. Larison, ed.), copyright 1992. These combinations are given by way of example only. Workers in the art can, by the straightforward procedures set forth herein, select and test other chromophores.

EXAMPLE 1

Initial Determination of Spectral Overlap

In order to determine the spectral overlap between the absorption spectrum of DABCYL and emission spectrum of each of several fluorophores, the absorption spectrum of DABCYL was determined. Since the absorption spectra of DABCYL may be altered upon attachment with DNA, we coupled DABCYL to an oligodeoxynucleotide by using methods described by Tyagi and Kramer 1996. The oligodeoxynucleotide was 5' AAG TTA AGA CCT ATG A-hexalkylamino-DABCYL SEQ ID NO:1. A $6 \times 10^{-6}$ M solution ($400\mu$) of this oligodeoxynucleotide was placed in a quartz cuvette and its absorption spectrum was determined using a Perkin-Elmer Lambda 3A UV-Visible spectrophotometer. The visible portion of this spectrum is shown in FIG. 3. The emission spectra of molecular beacons containing different fluorophores (each bound to their targets) is also plotted in the same figure. Each spectrum was normalized by assigning a value of 100 to its maxima and proportionally lower value to other points. For each emission spectrum, only the top 75% of the spectrum on either side of the maxima were considered. By "top 75%" is meant the range of emission wavelength for which the emission is at least 75% of the maximum emission. The extent of overlap between the absorption spectrum of DABCYL and the emission spectrum of various fluorophore was determined graphically. The spectral overlap for EDANS was, sum of absorption of DABCYL at each wavelength between 490 nm and 524 nm plus sum of emission of EDANS at each wavelength from 469 nm to 489 nm. For Fluorescein it was, sum of absorption of DABCYL at each wavelength between 507 nm and 527 nm plus sum of emission of Fluorescein at each wavelength from 505 nm to 530 nm. For Lucifer Yellow it was the sum of absorption of DABCYL at each wavelength between 506 nm and 548 nm plus the sum of emission of Lucifer Yellow at each wavelength from 520 nm to 504 nm. For BODIPY, Eosine, Erythrosine, and Tetramethylrhodamine the overlap was the sum of DABCYL absorption from 513 nm to 533 nm, 532 nm to 553 nm, 542 nm to 563 nm, and 560 nm to 588 nm respectively. For Texas Red (shown in FIG. 3) there was no overlap at all, even when the entire emission spectrum was considered. The extents of spectral overlaps, which according to our definition has no units, are shown in Table 1.

Calculation Expected Quenching Efficiencies

For a chemical moiety to serve as a quencher of a fluorophore by FRET, its absorption spectrum must overlap with the emission spectrum of the fluorophore (Stryer, L. 1978; Cantor and Schimmel 1980; and Selvin P. R. 1995). The efficiency of FRET (and therefore quenching) between a fluorophore and a quencher is linearly proportional to the spectral overlap between the absorption spectrum of the quencher and the emission spectrum of the fluorophore. This prediction from Forster's original theory of fluorescence resonance energy transfer was confirmed experimentally (Haugland et al. 1969) and has since been the basis of selection of FRET pairs. The expected efficiency or degree of quenching for the set of fluorophores, assuming a linear relationship between the quenching efficiency and the spectral overlap, are shown in Table 1. In order to calculate the expected efficiency or degree of quenching, the spectral overlap for each fluorophore was divided by the spectral overlap for EDANS and multiplied by the observed quenching efficiency of EDANS. The expected degrees of quenching are also presented in Table 1.

EXAMPLE 2

Synthesis of Molecular Beacons to Test the Degree of Quenching of Candidate Fluorophores by DABCYL We prepared eight molecular beacons with identical nucleotide sequences. Each molecular beacon contained a DABCYL moiety at its 3' end and one of six candidate fluorophores that we tested (Fluorescein, BODIPY, Lucifer Yellow, EDANS, Erythrosine, Eosine, Tetramethylrhodamine or Texas Red) at its 5' end. Thus they were identical except the nature of fluorophore that was present at their 5' end. In order to synthesize these molecules, an oligonucleotide which contained a protected sulphydryl group at its 5' end and a primary amino group at its 3' end was obtained from Midland Certified Reagents (Midland Tex.). The sulphydryl and the primary amino group in this oligonucleotide were tethered to the DNA via -(CH2)6- and -(CH2)7- spacers respectively. The sequence of the oligonucleotide was: 5' SH CCG AGA AAG AAA ATA TCA TTG GTG TTT CCT ATG ATG AAT CTC GG-Amino 3' SEQ ID NO:2. An amine reactive derivative of DABCYL was coupled to the 3' end of this oligonucleotide according to the methods described by Tyagi and Kramer 1996. The coupled oligonucleotide was purified using high pressure liquid chromatography. After purification, the protective group was removed from the sulphydryl group at the 5' end (Tyagi and Kramer 1996). This preparation was divided into seven fractions. These fractions were coupled with iodoacetamide derivatives of Fluorescein, Lucifer Yellow, EDANS, Erythrosine, Eosine and Tetramethylrhodamine and with the bromomethyl derivative of BODIPY (Molecular Probes). In each case, the unreacted fluorophore was removed by gel filtration on a small column (NP-5, Pharmacia). Each doubly labeled oligonucleotide was further purified by high pressure liquid chromatography and dissolved in buffer A (1 mM $MgCl_2$ and 20 mM Tris-HCl pH 8.0)

Determination of Quenching Efficiency

The molecular beacons labelled with DABCYL at their 3' ends and a fluorophore at their 5' ends were designed in such a way that six terminal nucleotides on either side of the molecule formed a hairpin stem which brought the fluorophore in close proximity to the DABCYL. With a FRET pair, it was expected from Tyagi et al. that quenching would occur by fluorescence resonance energy transfer. With non-FRET pairs, as defined herein, no quenching or less than minimally needed quenching was expected by fluorescence resonance energy transfer.

The middle region of these oligonucleotides constitutes a probe that can interact with a target. The interaction of the probe with a target leads to unwinding of the stem helix and separation of the fluorophore from the DABCYL by more than 100 Å. In this state, no fluorescence resonance energy transfer can occur and therefore no quenching can take place. Tyagi and Kramer have shown that when EDANS and DABCYL are used as a fluorophore and quencher of a FRET pair in these oligonucleotides, the fluorescence of EDANS is quenched very efficiently by DABCYL. Upon addition of the target of the molecular beacon the fluorescence of EDANS is fully restored.

In order to determine the degree of quenching for the present series of fluorophores, the excitation and emission spectra of each molecular beacon was recorded before and after addition of the target using a Photon Technology (Princeton) fluorometer. To obtain an emission spectrum solution of a molecular beacon in Buffer A was held at 25° C. in a cuvette. The solution was excited at the excitation maxima of the fluorophore in the molecular beacon, while the intensity of the emitted light was measured as a function of emission wavelength. An excitation spectrum was recorded by monitoring the intensity of emission at the emission maximum of the fluorophore and changing the excitation wavelength. Sufficient time was given for the hybrids to form. After recording the two spectra, a five-fold molar excess of the target of the Molecular Beacon was added to the solution. After the completion of hybridization, the excitation and emission spectra were recorded again. Four spectra were recorded for each of the eight Molecular Beacons. The spectra for two, Molecular Beacons containing EDANS and Tetramethylrhodamine, are shown in FIGS. 1–2, where the spectra before the addition of the target (71, 72, 73, 74) are depicted by broken lines and the spectra after the addition of target (1, 2, 3, 4) are shown by continuous lines. The spectra on the left are excitation spectra. On the right are emission spectra.

The degree of quenching was determined from the intensities of emission at the emission maxima. The percentage of observed quenching is defined as $(1-F_o/F_t)*100$, where $F_o$ is the intensity of emission before the addition of the target and $F_t$ is the intensity of emission after the addition of the target. Table 2 lists the observed quenching efficiency for each of the seven fluorophores tested, as well as the expected quenching efficiency if FRET was the mechanism.

EXAMPLE 3

In order to demonstrate the utility of fluorophore-quencher combinations that are available for use in probes of this invention, a multiplex detection assay utilizing four different nucleic acid targets was performed. We chose targets that differed in their nucleotide sequence by just one nucleotide and designed a set of four differently labeled molecular beacons to detect these targets. These molecular beacons possessed a DABCYL moiety at their 3' end and were identical in all respects, except that each was labeled with a different fluorophore at its 5' end and each had a different nucleotide at the center of its probe sequence. These molecular beacons were labeled with either a blue, green, orange, or red fluorophore and had either a thymidine, cytidine, adenine, or guanosine residue at the center of its probe sequence, respectively. The nucleotide sequences of the blue, green, orange, and red molecular beacons were Coumarin-5'-GCG AGC CAC CAA ATA TCA TAT GCT CGC-3'-DABCYL SEQ ID NO:3, Fluorescein-5'-GCG AGC CAC CAA ACA TGA TAT GCT CGC-3'-DABCYL SEQ ID NO:4, Tetramethylrhodamine-5'GCG AGC CAC CAA AAA TGA TAT GCT CGC-3'-DABCYL SEQ ID NO:5, and Texas red-5'-GCG AGC CAC CAA AGA TGA TAT GCT CGC-3'-DABCYL SEQ ID NO:6, respectively. The targets of these molecular beacons were 5'-AAA GAA AAT ATC ATA TTT GGT GTT TCC TAT-3' SEQ ID NO:7, 5'-AAA GAA AAT ATC ATG TTT GGT GTT TCC TAT-3' SEQ ID NO:8, 5'-AAA GAA AAT ATC ATT TTT GGT GTT TCC TAT-3' SEQ ID NO:9, 5'-AAA GAA AAT AT$\underline{C}$ ATC TTT GGT GTT TCC TAT-3' SEQ ID NO:10, respectively. The underlined residues represent the only difference in the nucleotide sequence among these molecules. The fluorophores were chosen in such a way that when each was excited at its optimal excitation wavelength and observed at its optimal emission wavelength, the fluorescence of one molecular beacon could be determined independently of the fluorescence of each of other molecular beacons. An equimolar mixture of these molecular beacons was prepared and aliquots of this mixture were plated into each of four tubes. One of the four targets was added to each of these solutions while holding the temperature of the solution 25° C., and the fluorescence of each molecular beacon in that tube was monitored repeatedly. The changes in fluorescence of each molecular beacon was monitored by rapidly changing the position of the diffraction gratings of our spectrofluorometer to alternate between the optional pairs of excitation and emission wavelengths for measuring the fluorescence of each fluorophore. While holding the excitation wavelength at 400 nm, the fluorescence of Coumarin was monitored at 475 nm for a five second interval. These wavelengths were changed to 491 and 515 for the next five seconds (Fluorescein), and then to 575 and 595 for the following five seconds (Tetramethylrhodamine), and finally to 595 and 615 for the last five seconds (Texas Red). This series of measurements was made repeatedly until the fluorescence of the perfectly matched probe-target hybrid reached a plateau. These results were plotted as, four separate fluorescence vs. time curves, one for each molecular beacon.

The addition of each target led to an increase in the fluorescence of the perfectly complementary molecular beacon, but did not lead to an increase in the fluorescence of the other molecular beacons that were present in the same solution (FIG. 7). When the target 100 contained an adenosine as its central nucleotide (Panel a), the blue fluorescence indicated by squares 101 increased, when the target 110 contained a guanosine as its central nucleotide (Panel b), the green fluorescence indicated by circles 111 increased, when the target 120 contained a thymidine as its central nucleotide (Panel c), the orange fluorescence indicated by inverted triangles 121 increased, and when the target 130 contained a cytidine as its central nucleotide (Panel d), the red fluorescence indicated by diamonds 131 increased. The color of the fluorescence in the tube indicated which nucleotide residue was present at the center of the target. There was no significant "crosstalk," either at the level of hybridization, or at the level of signal detection. The two notable exceptions were that a target 110 with a guanosine residue at its center elicited a small response 112 from a molecular beacon that contained a thymidine at the corresponding position, and a target 120 with a thymidine at its center elicited a small response 122 from a molecular beacon that contained a guanosine at the corresponding position. This occurred because guanosine is able to form a relatively stable base-pair with thymidine. Each target could also be identified visually by the color of the fluorescence that developed when higher concentrations of molecular beacons and targets were used and when the tubes were illuminated by a broad-wavelength ultraviolet lamp.

Figure 8A:
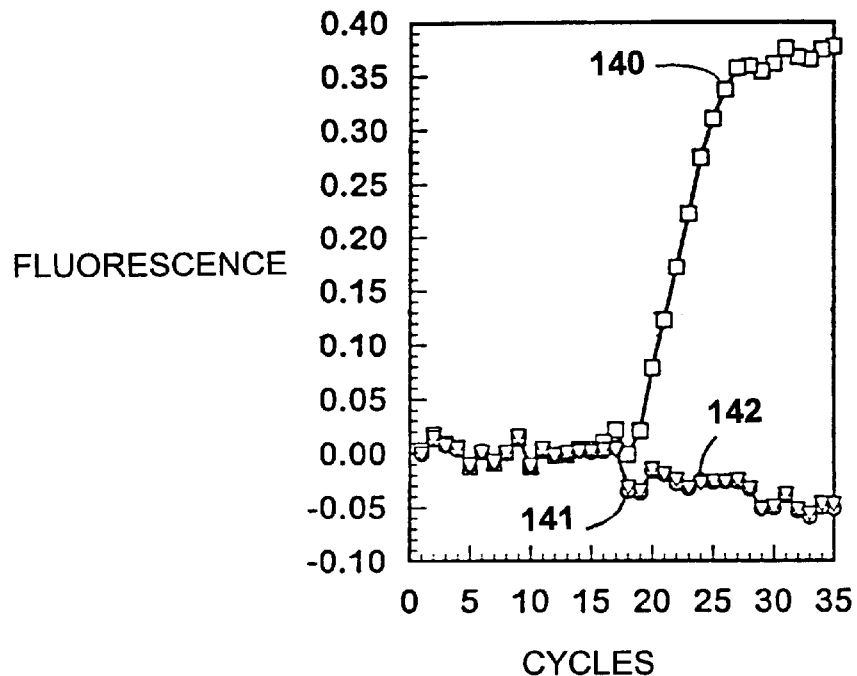
FIGS. 8A–8B shows real-time fluorescence measurements using two probes in a multiplex PCR amplification assay.
Figure 8B:
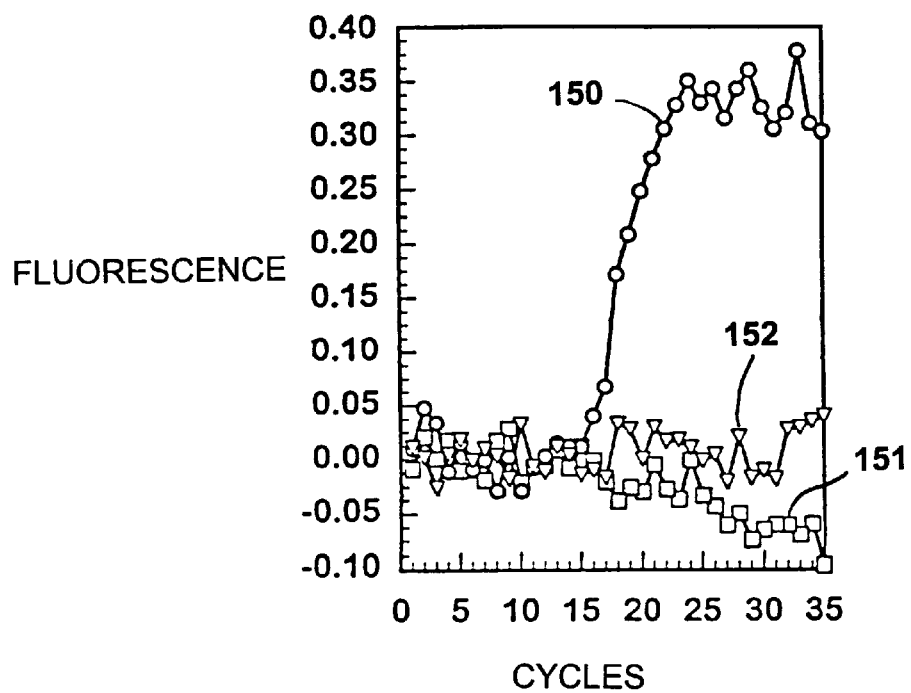

We also demonstrated the utility of this invention in a very simple detection of the genetic abnormality that is responsible for cystic fibrosis. One of the most common genetic causes of cystic fibrosis is a three-nucleotide deletion at position 508 in the gene for the cystic fibrosis transmembrane conductance regulator (CFTR). Two molecular beacons were prepared for the detection of this gene. One molecular beacon was labelled with Fluorescein and DABCYL and had a probe sequence that was perfectly complementary to the wild-type CFTR gene sequence. The other molecular beacon was labelled with Tetramethylrhodamine and DABCYL and had a probe sequence that was perfectly complementary to the mutant CFTR gene sequenced. Three tubes containing an equimolar mixture of both of these molecular beacons and containing the other components necessary for a polymerase chain reaction (including appropriate primers), were prepared. DNA encoding the wild-type gene was added to the first tube and DNA encoding the mutant gene was added to the second tube. The third tube was a negative control that did not contain any template DNA. Polymerase chain reactions were performed by cycling the temperature of the tubes between 94, 55 and 72 degrees centigrade corresponding to the melting, annealing, and polymerization steps, respectively, of the PCR cycle. The progress of the reactions was monitored in the sealed tubes during the course of these reaction by measuring the fluorescence of each molecular beacon repeatedly during the 55° cycle. A thermal cycler that could monitor the fluorescence of the sealed tubes in real-time was used for this purpose (System 7700, Applied Biosystems, Calif.). FIG. 8 shows the results. The tube that contained wild-type (template) DNA (Panel a) exhibited a rise in the fluorescence of the Fluorescein molecular beacon (squares 140), but did not exhibit a rise in Tetramethylrhodamine fluorescence (circles 141). The tube that received mutant template DNA (Panel b) exhibited a rise in the fluorescence of Tetramethylrhodamine (circles 150), but did not exhibit a rise in the fluorescence of Fluorescein (squares 151). The level of fluorescence of neither molecular beacon rose in the third tube. This background signal is indicated by inverted triangles 142,152 and is included in both of the panels. This experiment demonstrates that by using the fluorophore-quencher pairs selected according to this invention, it is possible to perform multiplex detection of genetic alleles.

EXAMPLE 4

Subsequent to our initial experiments on quenching according to the procedures set forth in Example 1 and Example 2, we carried out further experiments with more extensively purified Molecular Beacon probes. Three HPLC purifications were used for end-labeled Molecular Beacon probes having a central region 20 nucleotides long flanked by arms 6 nucleotides long and completely complementary to each other. Label pairs were DABCYL on one end and one of nine different fluorophores (FIG. 3) on the other end.

Expected quenching efficiency was calculated differently from the method of FIG. 2. Entire spectra were used as a basis, and calculation was according to Haugland et al. 1969, discussed earlier, wherein spectral overlap is defined as, $J=\int F(\lambda)\epsilon(\lambda)\lambda^4 d\lambda / \int F(\lambda) d\lambda$, where, $F(\lambda)$ is the normalized fluorescence emission at wavelength $\lambda$, and $\epsilon(\lambda)_4$ is the molar extinction coefficient of DABCYL when coupled to an oligonucleotide at wavelength $\lambda$. All spectral parameters were determined in the buffer mentioned above using a photon counting fluorometer (Photon Technology International, NJ).

Utilizing full spectra, of course, the amount of overlap is greater than the amount calculated according to Example 1, and, consequently, so is the expected quenching efficiency. Our definition of the minimum expected quenching efficiency required for a FRET pair and for a non-FRET pair useful in a probe according to this invention all change upwardly using this different technique. The minimum expected efficiency for a FRET pair would be 80%, for example (rather than 60% according to the method of Example 1), and a probe according to this invention would have observed quenching efficiency of at least 80%, preferably 90% and more preferably 95%, plus be at least 10% above the expected from overlap, preferably at least 15%. The results obtained are presented in Table 4. To avoid confusion, the entirety of this specification and claims, except for this Example 4, is to be interpreted according to the definitions related to the procedures of Examples 1 and 2, not this Example 4.

TABLE 4

Comparison of Expected and Observed Quenching Efficiency, %

| Fluorophore | Spectral Overlap ($10^{-15}M^{-1}cm^{-3}$) | Expected Quenching Efficiency, % | Observed Quenching Efficiency, % |
|---|---|---|---|
| Coumarin | 1.260 | 99.3 | 99.3 |
| EDANS | 1.090 | 85.9 | 99.5 |
| Fluorescein | 0.974 | 76.7 | 99.9 |
| Lucifer Yellow | 0.796 | 62.7 | 99.2 |
| BODIPY | 0.781 | 60.9 | 95.0 |
| Eosine | 0.414 | 32.9 | 98.2 |
| Erythrosine | 0.253 | 19.9 | 87.5 |
| Tetramethyl-rhodamine | 0.019 | 1.4 | 98.7 |
| Texas Red | 0.000 | 0.0 | 99.1 |

We claim:

1. A probe capable of hybridizing with a nucleic acid strand comprising one or two molecules containing nucleotides selected from the group consisting of natural nucleotides, modified nucleotides and combinations thereof, and a non-FRET label pair consisting of a first fluorophore and a chromophore, said chromophore selected from the group consisting of fluorophores and non-fluorescent quenchers, wherein interaction of the probe with a target causes the probe to change from a first conformation to a second conformation, thereby changing the distance between the labels of said label pair, and wherein in only one conformation do the labels touch sufficiently to quench the fluorescence of said first fluorophore by at least 25 percent.

2. The probe according to claim 1 wherein said probe comprises two molecules that are capable of hybridizing with one another to form a hybrid and one member of said label pair is attached to one of said molecules at an end of said hybrid, wherein the quenching efficiency in the hybrid is at least sixty percent and at least ten percent above the quenching efficiency expected based on spectral overlap.

3. The probe according to claim 1 wherein said probe comprises a single molecule.

4. The probe according to claim 3 wherein the members of said non-FRET label pair, when attached to end nucleotides of double stranded DNA hybridized to each other, provide a quenching efficiency of at least sixty percent and at least ten percent above the quenching efficiency expected based on spectral overlap.

5. The probe according to claim 4 wherein the members of said non-FRET label, when attached to end nucleotides of double stranded DNA hybridized to each other, provide a quenching efficiency of at least seventy percent and at least thirty percent above the quenching efficiency expected based on spectral overlap.

6. The probe of claim 5 wherein the choromophore is a non-fluorescent quencher.

7. The probe according to claim 6 wherein the quencher is DABCYL.

8. The probe according to claim 6 wherein said molecule is a self-hybridizing oligonucleotide having a target complementary region of 7–25 nucleotides flanked by arms hybridizable to one another to form a stem duplex 3–8 nucleotides in length.

9. The probe according to claim 5 wherein the chromophore is a second fluorophore having an excitation maximum at a wavelength shorter than the excitation maximum of said first fluorophore.

10. The probe of claim 5 wherein said molecule is a self-hybridizing oligonucleotide having a target complementary region of 7–140 nucleotides flanked by arms hybridizable to one another to form a hybrid 3–25 nucleotides in length.

11. The probe according to claim 3 comprising two non-FRET label pairs.

12. A kit of reagents for an assay comprising detection reagents that include a probe according to claim 1.

13. The kit according to claim 12 further comprising reagents for performing nucleic acid amplification.

14. The kit according to claim 13 wherein said amplification is selected from the group consisting of PCR, 3SR, LCR, Q-Beta replication and NASBA.

15. The kit according to claim 14 wherein said amplification is PCR.

16. The kit according to claim 12 wherein said probe comprises a single molecule; wherein the members of said non-FRET label pair, when attached to end nucleotides of double-stranded DNA hybridized to each other, provide a quenching efficiency of at least seventy percent and at least thirty percent above the quenching efficiency expected based on spectral overlap; and wherein the chromophore is a non-fluorescent quencher.

17. The kit according to claim 16 further comprising reagents for performing nucleic acid amplification.

18. The kit according to claim 17 wherein said amplification is PCR.

19. An assay that comprises detecting a target by contacting at least one probe according to claim 1 with a sample suspected of containing said target and measuring a change in fluorescence emission from said probe.

20. The assay according to claim 19, wherein the probe comprises a single molecule; wherein the members of said non-FRET label pair, when attached to end nucleotides of double-stranded DNA hybridized to each other, provide a quenching efficiency of at least seventy percent and at least thirty percent above the quenching efficiency expected based on spectral overlap; and wherein the chromophore is a non-fluorescent quencher.

21. The assay according to claim 20 that is a multiplex assay.

22. The assay according to claim 20 which includes amplification by PCR, and detection occurs in real time.

23. An assay that includes detection by contacting at least one single-stranded hybridization probe with a sample suspected on containing a target for said probe, and measuring an absorbance, said probe being a self-hybridizing oligonucleotide having a target complementary region of 7–140 nucleotides flanked by arms hybridizable to one another to form a hybrid 3–10 nucleotides in length, said probe containing nucleotides selected from the group consisting of natural nucleotides, modified nucleotides and combinations thereof, and each arm of said probe containing one of a pair of chromophores, wherein interaction of the probe with the target causes the probe to change from a first confirmation to a second confirmation, thereby increasing the distance between said chromophores, and wherein only in said first conformation do the chromophores touch sufficiently to detectably change absorbance.

24. The probe according to claim 1 wherein the label pair comprises a first fluorophore selected from the group consisting of Fluorescein, Lucifer Yellow, BODIPY, Eosine, Erythrosine, Tetramethylrhodamine, Texas Red and Coumarin, and a chromophore selected from the group consisting of DABCYL, DABMI, Malachite Green and Coumarin.

25. The kit according to claim 16 wherein said molecule is a self-hybridizing oligonucleotide having a target complementary region of 7–25 nucleotides flanked by arms hybridizable to one another to form a stem duplex 3–8 nucleotides in length.

26. The kit according to claim 12 wherein the label pair comprises a first fluorophore selected from the group consisting of Fluorescein, Lucifer Yellow, BODIPY, Eosine, Erythrosine, Tetramethylrhodamine, Texas Red and Coumarin, and a chromophore selected from the group consisting of DABCYL, DABMI, Malachite Green and Coumarin.

27. The assay according to claim 20 which includes amplification, and said target is a product of said amplification.

28. The assay according to claim 20 wherein the probe is a self-hybridizing oligonucleotide having a target complementary region of 7–25 nucleotides flanked by arms hybridizable to one another to form a stem duplex 3–8 nucleotides in length.

29. The assay according to claim 19 wherein the label pair comprises a first fluorophore selected from the group consisting of Fluorescein, Lucifer Yellow, BODIPY, Eosine, Erythrosine, Tetramethylrhodamine, Texas Red and Coumarin, and a chromophore selected from the group consisting of DABCYL, DABMI, Malachite Green and Coumarin.

30. An oligonucleotide probe comprising a) a stem duplex formed by a first fluorophore-labeled arm and a second chromophore-labeled arm, and b) a single-stranded loop joining said arms, wherein said first fluorophore and chromophore are a non-FRET pair which, when attached to end nucleotides of double-stranded DNA that are hybridized to each other, provide a quenching efficiency of at least sixty percent and at least ten percent above the quenching efficiency expected on the basis of spectral overlap, and wherein the fluorescence of said first fluorophore measured for the probe in the absence of a nucleic acid sequence complementary to said loop is at least twenty percent lower than measured for the probe in the presence of a five-fold molar excess of said nucleic acid sequence complementary to said loop.

31. The probe of claim 30 wherein said first fluorophore and chromophore are a non-FRET pair which, when attached to end nucleotides of double-stranded DNA that are hybridized to each other, provide a quenching efficiency of at least seventy percent and at least thirty percent above the quenching efficiency expected based on spectral overlap.

32. The probe of claim 31 wherein the fluorescence of said first fluorophore measured for the probe in the absence of a nucleic acid sequence complementary to said loop is at least forty percent lower than measured for the probe in the presence of a five-fold molar excess of said nucleic acid sequence complementary to said loop.

33. The probe according to claim 32 wherein said chromophore is a non-fluorescent quencher.

34. The probe according to claim 33 wherein said quencher is selected from the group consisting of DABCYL, DABMI and Malachite Green.

35. The probe according to claim 32 wherein said chromophore is a second fluorophore having an excitation maximum at a wavelength shorter than the excitation maximum of said first fluorophore.

36. The probe of claim 30, further comprising a tethering extension to at least one of said arms.

37. In an assay for detecting at least one target nucleic acid sequence, the improvement comprising generating a detectable signal by hybridizing the single stranded loop of the probe of claim 30 with said target nucleic acid sequence.

38. The assay of claim 37, wherein said assay includes nucleic acid amplification.

39. The assay of claim 38, wherein said amplification is a polymerase chain reaction.

40. The assay of claim 38, wherein said probe is added to said assay prior to amplification.

41. The assay of claim 37, the assay being a multiplex assay.

42. The assay of claim 37, wherein said first fluorophore and chromophore are a non-FRET pair which, when attached to end nucleotides of double-stranded DNA that are hybridized to each other, provide a quenching efficiency of at least seventy percent and at least thirty percent above the quenching efficiency expected based on spectral overlap, and wherein the fluorescence of said first fluorophore measured for the probe in the absence of a nucleic acid sequence complementary to said loop is at least forty percent lower than measured for the probe in the presence of a five-fold molar excess of said nucleic acid sequence complementary to said loop.

43. A kit of reagents comprising detection reagents including a probe of claim 30.

44. The kit of claim 43, further comprising reagents for performing nucleic acid amplification.

45. The kit of claim 44, wherein said amplification is selected from the group consisting of PCR, 3SR, LCR, Q-Beta replication, and NASBA.

46. The kit according to claim 45, wherein said amplification is PCR.

47. The kit according to claim 43, wherein said first fluorophore and chromophore are a non-FRET pair which, when attached to end nucleotides of double-stranded DNA that are hybridized to each other, provide a quenching efficiency of at least seventy percent and at least thirty percent above the quenching efficiency expected based on spectral overlap, and wherein the fluorescence of said first fluorophore measured for the probe in the absence of a nucleic acid sequence complementary to said loop is at least forty percent lower than measured for the probe in the presence of a five-fold molar excess of said nucleic acid sequence complementary to said loop.

* * * * *